United States Patent [19]
Bolsen

[11] Patent Number: 5,942,193
[45] Date of Patent: Aug. 24, 1999

[54] DAILY AIR REMOVAL TEST FOR STERILIZERS

[75] Inventor: Kathryn A. Bolsen, Mentor, Ohio

[73] Assignee: Steris Corporation, Mentor, Ohio

[21] Appl. No.: 08/882,666

[22] Filed: Jun. 25, 1997

[51] Int. Cl.⁶ .................................................. G01L 19/12
[52] U.S. Cl. .................... 422/119; 422/112; 422/296; 73/37; 73/49.3; 116/268; 116/272
[58] Field of Search .................... 422/112, 119, 422/113, 296, 292, 50, 55, 58, 61, 91; 73/744, 37, 49.3; 116/266, 268, 272

[56] References Cited

U.S. PATENT DOCUMENTS

| | | |
|---|---|---|
| 4,289,088 | 9/1981 | Scibelli . |
| 5,200,147 | 4/1993 | Augurt .................................. 422/58 X |
| 5,404,746 | 4/1995 | Ocker ................................... 116/266 X |
| 5,659,295 | 8/1997 | Renfroe et al. . |
| 5,677,492 | 10/1997 | Huang . |

*Primary Examiner*—Krisanne Thornton
*Assistant Examiner*—E. Leigh McKane
*Attorney, Agent, or Firm*—Fay, Sharpe, Beall, Fagan, Minnich & McKee

[57] ABSTRACT

A device for evaluating air removal is subjected to a sterilization process whose effectiveness is dependent on a sufficiently high vacuum being achieved. A closure or lid (20, 70) seals an opening into an interior chamber (12) of a container (10). The closure and container are mechanically interconnected, e.g., fricitonally, such that a preselected pressure differential across the closure is needed to release the closure. The friction or other mechanical interconnection level and a pressure in the interior chamber are selected such that when the exterior of the container is subject to a preselected vacuum, the closure releases. Ease or reliability of reading the indication is improved with a spring (50) for expelling the closure or a frangible member (56, 72) which is severed or irreversibly deformed as the closure releases.

19 Claims, 1 Drawing Sheet

DAILY AIR REMOVAL TEST FOR STERILIZERS

BACKGROUND OF THE INVENTION

The present invention relates to the sterilization arts. It finds particular application in conjunction with the assessment of evacuation in vaporized hydrogen peroxide sterilization systems, and will be described with particular reference thereto. It should be appreciated, however, that the invention is also applicable to other processes where evacuation is monitored on a frequent basis.

Sterilization and reuse of instruments has proved to be a valuable means of cutting the costs of delivering health care. Hydrogen peroxide vapor is a particularly useful sterilant for instruments because of its effectiveness at low temperatures, which avoids destruction of heat-sensitive medical instruments. In addition, it decomposes to water and oxygen, which are not harmful and do not pose disposal problems.

In use, hydrogen peroxide vapor is mixed with water vapor. At the temperatures employed for hydrogen peroxide sterilization, the water vapor does not act as an effective sterilant. Because it diffuses more rapidly into narrow lumens and other difficult to reach areas of instruments than hydrogen peroxide vapor, the effectiveness of hydrogen peroxide as a sterilant is often reduced by the presence of water vapor. Moreover, condensed water acts as a shield for microorganisms beneath its surface, further reducing the effectiveness of the sterilant.

Evacuation of the sterilizer at various times throughout the sterilization process has been shown to overcome these problems and result in effective sterilization of even the most challenging of instruments. Cyclic evacuation during a cycle tends to pump the vapor down lumens and narrow passages. Evacuation of the sterilization chamber prior to a sterilization cycle also permits the sterilant to diffuse rapidly throughout the chamber and allows greater concentrations of sterilant to be achieved at a given pressure. This increases the rate of contact of the sterilant with the instruments, thereby reducing the time required for effective sterilization.

Since the effectiveness of sterilization depends heavily on the ability of the sterilizer to draw a sufficiently low vacuum, it is important to monitor the sterilizer for leaks on a regular basis, preferably at least once a day. Pressures as low as about 0.5 Torr are currently employed in commercial hydrogen peroxide vapor sterilization systems. Regular confirmatory monitoring assures that the purported sterilization has occurred, or at least that there was not a failure.

Current methods of monitoring the pressure reached within a sterilization chamber involve the use of fairly expensive equipment which, although accurately monitoring operational parameters, often does not provide an easy to read check on the adequacy of the vacuum.

The present invention provides a new and improved device for air removal testing of sterilization or disinfection systems which overcomes the above-referenced problems and others.

SUMMARY OF THE INVENTION

In accordance with one aspect of the present invention, a device for air removal testing of sterilization and disinfection systems is provided. A container includes an interior chamber and an exterior. The container includes a base and sides, sealed to the base, and an opening into the chamber. A lid, constructed to seal the opening in the chamber, seals the chamber until a preselected reduction in the pressure surrounding the container causes the lid to be expelled from the chamber. A gas is disposed within the chamber.

In accordance with another aspect of the present invention, a method for the assessing air removal from gaseous sterilization or disinfection systems is provided. An interior chamber of a container is sealed with a closure such that (i) the container and closure have a level of mechanical interaction and (ii) the interior chamber has a selected internal pressure. The level of mechanical interaction and the internal pressure are selected such that the closure releases at a preselected vacuum.

The container is subjected to a sterilization or disinfection process in which air is removed to subject the container and items to be sterilized or disinfected to a preselected vacuum. The closure is observed. Release of the closure indicates that the preselected vacuum was obtained.

One advantage of the present invention is that it provides an inexpensive method of determining the adequacy of the vacuum drawn in a sterilization chamber.

An other advantage of the present invention is that it provides a rapid method of checking for leaks in a sterilization chamber.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
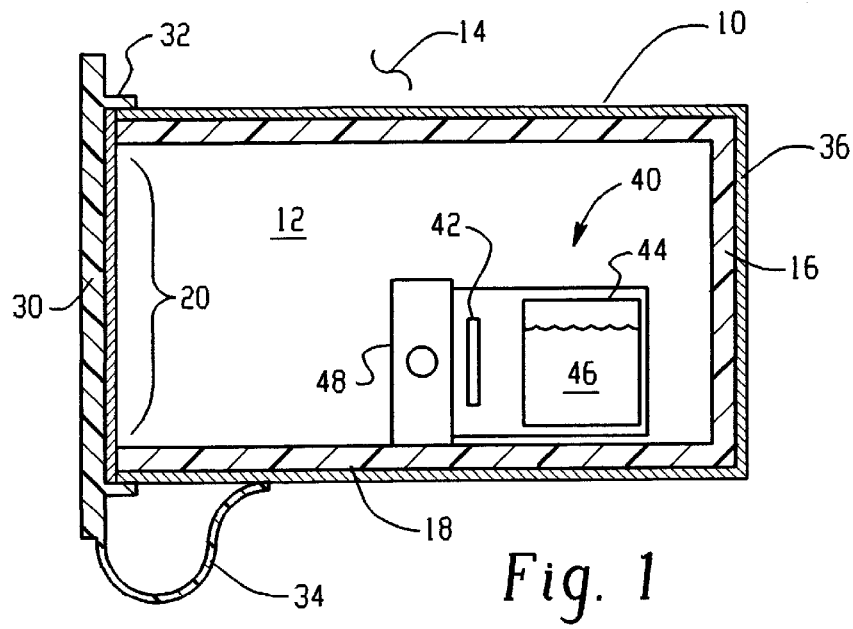
FIG. 1 is a cross sectioned view of a daily air removal test device for determining whether a sufficient vacuum is drawn in a sterilization chamber of the present invention.

With reference to FIG. 1, a container 10 defines an interior chamber 12 and an exterior 14. The container has a base 16 and sides 18. The sides 18 are sealed to the base 16 to prevent leakage of gas from the chamber 12 when the device is exposed to a high vacuum. The container 10 includes an opening 20. A closure, such as a lid or top 30, is constructed to cover the opening 20 and to seal the chamber 12.

The container 10 and lid 30 are preferably constructed of materials that are not subject to degradation under the sterilization conditions employed in the sterilization chamber to be evaluated. For use in hydrogen peroxide vapor sterilizers, an inexpensive plastic, such as a rigid polypropylene is particularly preferred.

The lid 30 preferably includes a lip 32 constructed to overhang the exterior of the sides 18 of the container 10 and thereby seal the chamber when the lid is pressed firmly against the container opening 20. However, other methods of providing a releasable seal between the lid and the container are also contemplated. Preferably, a flexible strip 34 connects the lid 30 to the exterior of the container 10 to prevent the lid 30 and chamber 10 from being disassociated in use.

The interior chamber 12 contains a gas such as air at a selected pressure. The device operates due to a pressure differential between the interior chamber 12 and the exterior 14 of the container. With the lid 30 releasably sealing the container opening 20, the device is placed in a sterilization chamber to be evaluated. When a vacuum is drawn in the sterilization chamber around the device, the difference in pressure causes the lid 30 to pop off the container 10. This opening of the device provides a simple method for detecting whether a sterilizaton chamber has undergone evacuation. Preferably, the lid 30 and the container 10 are constructed so that the lid is held in position over the chamber opening 20 until a preselected vacuum is drawn in the sterilization chamber, sufficient to enable effective sterilization conditions to be achieved.

The selection of the closure mechanism for the lid 30 in combination with the selection of the interior gas pressure sets the external pressure at which the lid will pop off. The lid 30 is held on the container 10 by a combination of interior/exterior pressure differential and mechanical friction. Optionally, other weak mechanical engagements, such as a heat seal, adhesive, chemical bond, weakened zone, or the like may also be utilized. In one example, the lid 30 is connected to the container with a mechanical engagement, e.g., friction between lip 32 and the sides 12, that yields with a pressure differential of 1.0 Torr (a relatively weak engagement). To design a release at 0.5 Torr, for example, the lid is placed on the container in a vacuum drawn to 1.5 Torr. In this manner, the container interior 12 is drawn to a low vacuum which holds the lid firmly on the container near atmosphere pressures. However, when the vacuum outside of the container is lower that the pressure in the chamber by the frictional engagement, the higher pressure within the chamber successfully pushes or pops the lid off. In the present example, below 0.5 Torr, the 1.5 Torr pressure in the container overcomes the 1.0 Torr's worth of friction and pushes the lid off.

For a stronger mechanical connection between the lid and the container, an interacting rib and groove arrangement is provided. That is, the lip 32 has an inward facing rib and the container has a mating outward facing groove. The size and shape are selected such that with the interior of the container at a relatively high pressure, e.g., atmospheric, the mechanical engagement, e.g., friction, is not overcome until the exterior pressure drops to the preselected pressure, e.g., 0.5 Torr. Again, heat seals, adhesive, weakened zones, chemical bonds, a combination of any of these, and the like can be utilized to provide the calibrated mechanical engagement.

When the selected pressure in the chamber 10 is above or below atmospheric pressure, the container is preferably constructed of a material that is impermeable to gases to prevent diffusion from, or into, the chamber. Alternately, an interior lining or external coating 36 of an impermeable material such as aluminum is used to prevent gaseous diffusion. The gas used within the chamber 10 is preferably one which does not undergo a vapor-to-liquid transition at the temperatures experienced prior to, or during the sterilization process. When the gas is air, the air is preferably dehumidified prior to filling the container to eliminate differences in ambient humidity that could cause pressure differences in the chamber due to subsequent condensation of water vapor.

Optionally a series of devices, each one calibrated to release the lid at a different, selected vacuum pressure, are used to determine the vacuum drawn in the sterilization chamber within a limited range.

In one preferred embodiment, a chemical or biological indicator 40 is disposed in the interior 12 of the chamber 10.

The indicator 40 detects whether conditions for the effective sterilization of instruments have been met. Moreover, because the indicator 40 remains sealed within the device unless the lid 30 pops from the chamber 10, the indicator will only indicate successful sterilization if it has been exposed to sterilant after the required level of evacuation has been achieved. The use of an indicator sealed in the device therefore provides a method for detecting whether a sufficient vacuum was drawn during a sterilization process to allow the sterilant subsequently to penetrate and sterilize lumens and other hard to reach areas of instruments.

A preferred indicator 40 is a self-contained biological indicator. The indicator includes a disc 42 of paper or other suitable material. A calibrated population of a microorganism that exhibits a high resistance to the sterilization process is disposed on the disc 42. A sealed ampule 44, disposed within the indicator 40 contains a nutrient medium 46 capable of sustaining growth of viable microorganisms. The indicator 40 is constructed such that during the sterilization cycle, sterilant passes through the indicator and comes into contact with the microorganisms on the disk 42. After completion of the sterilization process, a cap 48 seals the indicator and simultaneously breaks the ampule 46, allowing the nutrient medium 46 to come into contact with the microorganisms. Growth of remaining viable microorganisms is detected, preferably within one week or less.

Figure 2:
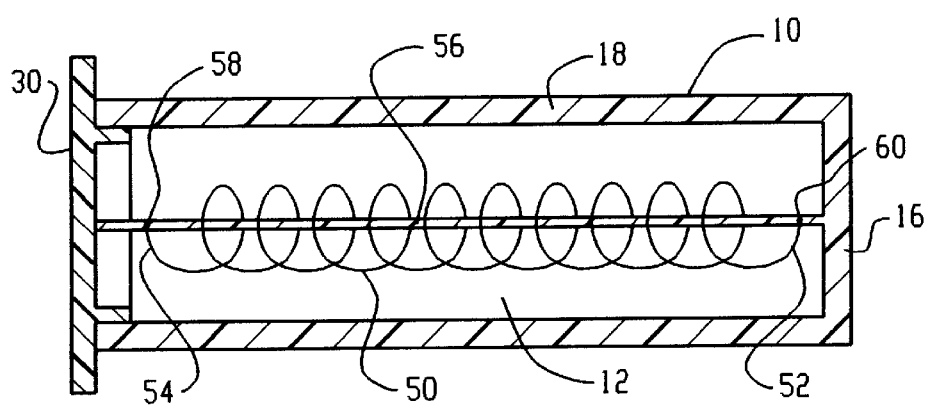
FIG. 2 is a cross section of an alternative embodiment of a test device of the present invention; and, FIG. 3 is a cross section of a second alternative embodiment of a test device of the present invention.

With reference to FIG. 2, the device optionally includes a spring 50, including two ends 52 and 54, disposed under compression within the chamber 10. When the lid 30 is released from the chamber 10, the tension in the spring causes the end 54 to extend beyond the opening 20 in the chamber 10. Preferably, the end 52 of the spring 50 is connected to the sides 18 or base 17 of the chamber 10, thereby preventing the spring from falling out of the chamber when the lid 30 is released from the opening 20. The spring 50 serves to prevent the lid 30 from reconnecting with the chamber 10 after its release, which would give an incorrect indication that the required vacuum has not been reached in the sterilization chamber. As a further indication that sufficient vacuum has been drawn to pop the lid 30 from the chamber 10, a post or rod 56 is optionally connected at two positions 58 and 60 to the spring 50 such that the release of the lid 30 causes the spring to extend, creating sufficient tension in the post 56 to snap the post, thereby providing a permanent and readily observable record that the required vacuum has been obtained.

Figure 3:
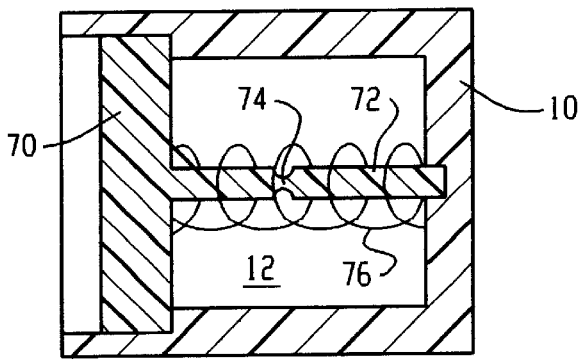

With reference to FIG. 3, a closure, such as a piston member 70, is slidably received in the interior 12 of the container 10. The piston is held in place by an elongated element 72 and, preferably a vacuum within the chamber. The elongated element has a weakened zone 74 sized to fail with a preselected pressure differentiation across the piston. Alternately, the mechanical member can irreversibly deform in other ways, such as stretching, delaminating, unfolding, or the like. Preferably, a spring 76 insures that once the weakened zone fails, the piston is ejected from the chamber.

On removal of the device from the sterilization chamber, the new position of the piston 70 gives a rapid indication that the required evacuation pressure has been reached during the sterilization process. Preferably, the canister 10 is constructed of a material that does not degrade appreciably during the sterilization process. In another embodiment, the sides 18 of the canister are constructed of a material which permits the position of the piston 70 to be visible through the canister sides. This allows movement of the piston 70 and severance of the elongated element to be detected even without ejecting the piston from the container.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A device for air removal testing of sterilization or disinfection systems, the device comprising:

a) a container defining an internal chamber and an exterior, the container including hermetically sealed base and side walls and a single opening into the chamber, the base and side walls being sealed to each other;

b) a lid releasably attached to the container base and side walls to seal the opening in the chamber such that the internal chamber of the container is hermetically sealed from an ambient environment surrounding the container;

c) a gas sealed within the internal chamber, such that as vacuum in the ambient environment increases, the gas in the internal chamber urges the lid to detach from the container with an increasing force; and, d) a mechanical interconnection between the lid and the container which inhibits the lid from detaching from the container, the mechanical interconnection being calibrated to allow the lid to detach from the container in response to a preselected force applied by the gas, which preselected force is calibrated to a preselected vacuum in the ambient environment, whereby detachment of the lid indicates that the ambient environment has reached the preselected vacuum.

2. The device of claim 1, wherein the container is constructed of materials that are resistant to degradation by a sterilization process.

3. The device of claim 2, wherein the container is constructed of a rigid polypropylene.

4. The device of claim 1, wherein the container is gas impermeable.

5. The device of claim 1, wherein the opening in the chamber is defined by the side wall of the container and wherein the lid includes a lip, the lip being constructed to overhang the side wall of the container and seal the opening.

6. The device of claim 1, wherein a flexible strip connects the lid to the container to prevent the lid and container from being disassociated when the lid is detached.

7. The device of claim 1, wherein a pressure of the gas within the chamber and the container and lid are interconnected such that the lid is not detached from the chamber until the exterior pressure drops below 1 Torr.

8. The device of claim 1, further including:

a sterilization indicator disposed in the interior chamber, such that the sterilization indicator is shielded from sterilant gases until the lid is expelled.

9. The device of claim 1, further including:

a spring disposed under compression in the interior chamber, expansion of the spring preventing reconnection of the lid to the container after the lid is detached.

10. A device for air removal testing of sterilization or disinfection systems, the device comprising:

a) a container defining an internal chamber and an exterior, the container including base and side walls and a single opening into the chamber, the base and side walls being sealed to each other, the chamber being lined with a gas-impermeable layer;

b) a lid, the lid releasably mounted to the container base and side walls to seal the opening in the chamber such that the internal chamber of the container is hermetically sealed from an ambient environment surrounding the container until a preselected reduction in pressure surrounding the chamber causes the lid to be expelled from the chamber; and c) a gas sealed within the internal chamber, such that as vacuum in the ambient environment increases, the gas in the internal chamber urges the lid to detach from the container with an increasing force.

11. A device for air removal testing of sterilization or disinfection systems, the device comprising:

a) a container including an internal chamber and an exterior, the container including base and side walls and an opening into the chamber, the base and side walls being sealed to each other;

b) a lid releasably mounted to the container base and side walls to seal the opening in the chamber such that the internal chamber of the container is hermetically sealed from an ambient environment surrounding the container until a preselected reduction in pressure surrounding the chamber causes the lid to be expelled from the chamber;

c) a gas sealed within the internal chamber, such that as vacuum in the ambient environment increases, the gas in the internal chamber urges the lid to detach from the container;

d) a spring disposed under compression in the interior chamber, expansion of the spring preventing reconnection of the lid to the container after the lid is detached; and, e) a mechanical element connected to the spring at two positions, the mechanical element being configured such that expansion of the spring causes the mechanical element to break, the mechanical element inhibiting the spring from biasing the lid until the lid is detached.

12. An indicator device for indicating whether a gaseous sterilant sterilization system has reached a preselected vacuum level during a sterilization cycle, the indicator device comprising:

a container defining an interior chamber that contains gas at a present pressure level;

a closure connected with the container with a preset level of mechanical interconnection, the preset pressure level and the preset mechanical interconnection level being set such that the closure is released at the preselected vacuum level; and, a spring disposed in the interior chamber biasing the closure to release.

13. The indicator device of claim 12 further including a severable mechanical element which is deformed as the closure is released, the severable mechanical element being disposed within the interior chamber.

14. An indicator device for indicating whether a gaseous sterilant sterilization system has reached a preselected vacuum level during a sterilization cycle and for detecting whether adequate sterilization conditions have been achieved after the preselected vacuum has been reached, the indicator device comprising:

a container defining an interior chamber that contains gas at a preset pressure level;

a closure connected with the container with a preset level of mechanical interconnection, the preset pressure level and the preset mechanical interconnection level being set such that the closure is released at the preselected vacuum level; and, a sterilant indicator disposed in the interior of the chamber such that the gaseous sterilant reaches the indicator only after the closure is released, whereby the sterilant indicator indicates inadequate sterilization if the preselected vacuum is not attained.

15. A method for assessing air removal from gaseous sterilization or disinfecting systems, the method comprising:
   a) sealing an interior chamber of a container with a closure such that (i) the container and the closure have a selected level of mechanical interaction and (ii) the interior chamber has a selected internal pressure which is independent of an exterior pressure, the level of mechanical interaction and the internal pressure being selected such that the closure releases at a preselected vacuum;
   b) subjecting the container to a sterilization or disinfection process in which air is removed to subject the container and items to be sterilized or disinfected to the preselected vacuum;
   c) observing whether the closure has been released as an indication of whether the preselected vacuum was attained.

16. The method of claim 15 further including:
as the closure is released expelling the closure with a compressed mechanical element.

17. The method of claim 15 further including:
as the closure is released, severing a frangible element to provide a positive indication that the preselected vacuum was attained.

18. The method of claim 15 further including:
disposing a plurality of containers, each constructed to release its closure at a different vacuum with the items to be sterilized or disinfected.

19. A method for assessing air removal from gaseous sterilization or disinfecting systems and for determining whether adequate sterilization has been achieved, the method comprising:
   a) sealing an interior chamber of a container with a closure such that (i) the container and the closure have a selected level of mechanical interaction and (ii) the interior chamber has a selected internal pressure which is independent of an exterior pressure, the level of mechanical interaction and the internal pressure being selected such that the closure releases at a preselected vacuum, an indicator which indicates exposure to sterilant or disinfectant gas being disposed within the chamber;
   b) subjecting the container to a sterilization or disinfection process in which includes:
      removing air to subject the container and items to be sterilized or disinfected to the preselected vacuum, and then
      subjecting the container and the items to a sterilant or disinfectant gas to sterilize the items;
   c) observing whether the closure has been released as an indication of whether the preselected vacuum was attained; and
   d) evaluating the indicator for exposure to sterilant gas.

* * * * *